US006559171B1

(12) United States Patent
Mitch et al.

(10) Patent No.: US 6,559,171 B1
(45) Date of Patent: May 6, 2003

(54) 7-OXO-2-AZABICYCLO[2.2.1]HEPTANES AS SELECTIVE MUSCARINIC RECEPTOR ANTAGONIST

(75) Inventors: Charles Howard Mitch, Columbus, IN (US); Steven James Quimby, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/980,261

(22) PCT Filed: May 26, 2000

(86) PCT No.: PCT/US00/09825

§ 371 (c)(1),
(2), (4) Date: Nov. 1, 2001

(87) PCT Pub. No.: WO00/75140

PCT Pub. Date: Dec. 14, 2000

Related U.S. Application Data

(60) Provisional application No. 60/137,770, filed on Jun. 4, 1999.

(51) Int. Cl.$^7$ ..................... A61K 31/439; C07D 417/12
(52) U.S. Cl. ...................... 514/362; 546/183; 514/299; 548/135
(58) Field of Search .................. 548/135; 514/362, 514/299; 546/183

(56) References Cited

U.S. PATENT DOCUMENTS

| | | |
|---|---|---|
| 5,134,146 A | 7/1992 | Showell et al. ............. 514/299 |
| 5,405,853 A | 4/1995 | Baker et al. ................. 514/299 |
| 5,646,289 A | 7/1997 | Alt et al. |
| 5,665,745 A * | 9/1997 | Alt et al. .................... 514/365 |
| 5,672,709 A | 9/1997 | Alt et al. |
| 5,821,371 A | 10/1998 | Alt et al. |
| 5,834,458 A | 11/1998 | Mitch |
| 5,889,019 A | 3/1999 | Mitch |
| 5,929,247 A | 7/1999 | Alt et al. |
| 5,998,434 A | 12/1999 | Mitch et al. |
| 6,124,312 A | 9/2000 | Mitch et al. |

FOREIGN PATENT DOCUMENTS

| | | |
|---|---|---|
| EP | 0 776 891 A1 | 11/1995 |
| EP | 0 776 896 A1 | 11/1995 |
| EP | 0 709 381 A | 5/1996 |
| WO | WO 97/19669 | 11/1995 |
| WO | WO 97/19944 | 11/1995 |
| WO | WO 97/20556 | 12/1995 |
| WO | WO 97/20561 | 12/1995 |
| WO | WO 98/46227 | 4/1997 |
| WO | WO 97/20819 A | 6/1997 |
| WO | WO 97/40016 A | 10/1997 |

OTHER PUBLICATIONS

Ward et al: 1,2,5–Thiadiazole Analogues of Aceclidine as Potent $m_1$ Muscarinic Agonists, *J. Med. Chem.*, 1998, 41, pp. 379–392.
Pombo–Villar et al: Absolute Configuration of 2–Substituted 2–Azabicyclo[2.2.1]hept–5–enes, *Helvetica Chimica Acta*, vol. 76 (1993), pp. 1203–1215.
Pombo–Villar, et al: 6–Carboxymethyl–2–azabicyclo[2.2.1] Heptane Enantiomers: Muscarinic Activities of Rigid Analogues of Arecoline, *Bioorganic & Medicinal Chemistry Letters*, vol. 2, No. 5, pp. 501–504, 1992.
Buckley, et al: Antagonist Binding Properties of Five Cloned Muscarinic Receptors Expressed in CHO–K1 Cells, *Molecular Pharmacology*, vol. 35, pp 469–476, 1989.
Hulme, et al: Muscarinic Receptor Subtypes, *Annual Rev. Pharmacol. Toxicol.* vol. 30, pp 633–733, 1990.
Shannon et al, In Vivo Pharmacology of Butylthio[2.2.2] (LY297802/NNC11–1053), An Orally Acting Antinociceptive Muscarinic Agonist, *Life Sciences*, vol. 60, Nos. 13/14, pp 969–976, 1997.
Bymaster et al: Potential Role of Muscarinic Receptors in Schizophrenia, *Life Sciences*, vol. 64, Nos. 6/7, pp. 524–534, 1999.

* cited by examiner

Primary Examiner—Joseph K. McKane
Assistant Examiner—Rebecca Anderson
(74) Attorney, Agent, or Firm—David M. Stemerick

(57) ABSTRACT

The present invention relates to muscarinic receptor modulators, specifically, 7-oxo-2-azabicyclo[2.2.1]heptanes of formula (I) which are useful for the treatment of various diseases and conditions, for example, Alzheimer's disease, glaucoma, psychosis, particularly schizophrenia or schizophreniform conditions, mania, pain, bipolar disorder, depression, sleeping disorders, epilepsy, gastrointestinal motility disorders, urinary incontinence, and cognition enhancement.

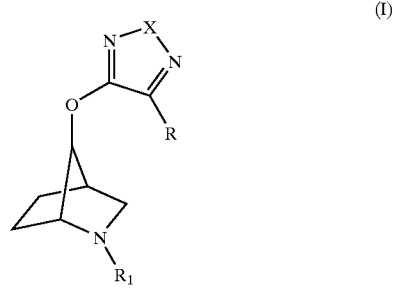

(I)

9 Claims, No Drawings

7-OXO-2-AZABICYCLO[2.2.1]HEPTANES AS SELECTIVE MUSCARINIC RECEPTOR ANTAGONIST

This is a 371 of PCT/US00/09825 filed May 26, 2000 which claims priority to U.S. Provisional Application No. 60/137,770 filed Jun. 4, 1999.

The present invention relates to therapeutically active 7-oxo-2azabicyclo[2.2.1]heptanes, the compounds of formula I, and pharmaceutical compositions thereof. The compounds of formula I are muscarinic receptor modulators. More specifically, the compounds of the present invention are agonists of the muscarinic M-4 receptor. As such they are useful for the treatment of various diseases and conditions. The present invention relates to the use of the compounds of formula I to treat diseases and conditions treated by muscarinic receptor modulators, for example, Alzheimer's disease, glaucoma, mania, bipolar disorder, depression, sleeping disorders, epilepsy, gastrointestinal motility disorders, urinary incontinence, pain, psychosis, particularly schizophrenia or schizophreniform conditions, and cognition enhancement, such as enhancement of learning, association, consolidation, and recognition. The present invention also relates to processes for the preparation of the compounds of formula I and intermediates thereof.

Compounds which interact with muscarinic receptors are known in the art. In particular, certain oxo-2-azabicycloalkane containing compounds are described as muscarinic receptor modulators in PCT Publication No. WO 96/12711, published May 2, 1996.

The present invention relates to compounds of formula I

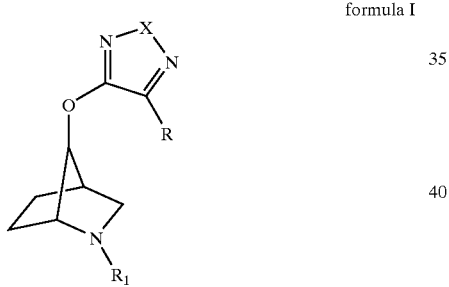

formula I wherein
- X is oxygen or sulfur;
- R is hydrogen, phenyl, substituted phenyl, —OR$_2$, —SR$_2$, —SOR$_2$, —SO$_2$R$_2$
  wherein R$_2$ is C$_1$–C$_{10}$ alkyl, C$_3$–C$_{10}$ alkenyl, C$_3$–C$_{10}$ alkynyl, substituted with from 1 to 3 substituents selected from the group consisting of hydrogen, halogen, —CF$_3$, —CN, phenyl, substituted phenyl, phenoxy, substituted phenoxy, thiophenoxy, substituted thiophenoxy, C$_3$–C$_8$ cycloalkyl, heterocycle, and —Z-heterocycle, wherein Z is oxygen or sulfur;
- R$_1$ is selected from the group consisting of hydrogen, C$_1$–C$_5$ alkyl, C$_2$–C$_5$ alkenyl and C$_2$–C$_5$ alkynyl;

or a pharmaceutically acceptable salt thereof.

Also, the present invention provides pharmaceutical compositions comprising a compound of formula I and a pharmaceutically acceptable diluent.

The present invention further provides a method of treating diseases and conditions treated by muscarinic receptor modulators in a patient in need thereof comprising administering to the patient an effective amount of a compound of formula I or pharmaceutically-acceptable addition salt thereof. Such diseases and conditions treated by muscarinic receptor modulators include Alzheimer's disease, glaucoma, mania, bipolar disorder, depression, sleeping disorders, epilepsy, gastrointestinal motility disorders, urinary incontinence, pain, psychosis, particularly schizophrenia or schizophreniform conditions, and cognition enhancement, such as enhancement of learning, association, consolidation, and recognition. Since the present compounds are muscarinic M-4 agonists they are particularly useful for treating pain and Alzheimer's disease and providing cognitive enhancement.

As used herein, the following terms have the meanings indicated:

the term "substituted phenyl" refer to a radical of the formula

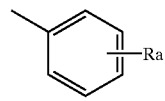

wherein Ra is from 1 to 2 substituents independently selected from the group consisting of hydrogen, halogen, C$_1$–C$_5$ alkyl, C$_1$–C$_5$ alkoxy, C$_1$–C$_5$ thioalkoxy, —CF$_3$, —CN, and phenyl;

the term "halogen" refers to a chlorine atom, bromine atom, or an iodide atom;

the term "C$_1$–C$_{10}$ alkyl" refers to a straight or branched chain alkyl having from one to ten carbon atoms and includes, methyl, ethyl, n-propyl, iso-propyl, n-butyl, sec-butyl, iso-butyl, t-butyl, pentyl, hexl, heptyl, octyl, nonyl, decyl, and the like;

the term "C$_3$–C$_{10}$ alkenyl" refers to a straight or branched chain alkenyl having from three to ten carbon atoms containing at least one double-bond and includes, allyl, but-2-enyl, but-3-enyl, 3-methylbut-3-enyl, pent-2-enyl, pent-3-enyl, pent-4-enyl, hexenyl, heptenyl, octenyl, nonenyl, docenyl, and the like;

the term "C$_3$–C$_{10}$ alkynyl" refers to an unsaturated branched or linear group having from three to ten carbon atoms and at least one triple bond and includes, propargyl, but-2-ynyl, but-3-ynyl, pentynyl, hexynyl, heptynyl, octynyl, nonynyl, decynyl and the like;

the term "C$_3$–C$_8$ cycloalkyl" refers to a saturated or unsaturated cyclic alkyl group having from three to eight carbon atoms and from 1 to 2 substituents independently selected from the group consisting of hydrogen, halogen, C$_1$–C$_5$ alkyl, C$_1$–C$_5$ alkoxy, C$_1$–C$_5$ thioalkoxy, —CF$_3$, —CN, and phenyl and includes, cyclopropyl, cyclobutyl, cyclopentyl, cyclohexyl, cycloheptyl, cyclooctyl, cyclopentenyl, cyclohexenyl and the like, and includes cylcoalkyl groups in which one of the carbon atoms of the cycloalkyl is part of the C$_1$–C$_{10}$ alkyl, C$_3$–C$_{10}$ alkenyl, or C$_3$–C$_{10}$ alkynyl to which it is attached and includes cyclic alkyl groups having a fused phenyl group as part of the ring;

the term "substituted phenoxy" refers to a radical of the formula

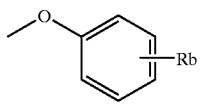

wherein Rb is from 1 to 2 substituents independently selected from the group consisting of hydrogen, halogen, $C_1$–$C_5$ alkyl, $C_1$–$C_5$ alkoxy, $C_1$–$C_5$ thioalkoxy, —$CF_3$, —CN, and phenyl;

the term "substituted thiophenoxy" refers to a radical of the formula

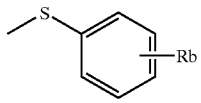

wherein Rb is from 1 to 2 substituents independently selected from the group consisting of hydrogen, halogen, $C_1$–$C_5$ alkyl, $C_1$–$C_5$ alkoxy, $C_1$–$C_5$ thioalkoxy, —$CF_3$, —CN, and phenyl;

the term "heterocycle" refers to a 5 or 6 membered heterocyclic group containing from one to four heteroatoms independently selected for the group consisting of N, O, and S atom(s), which heterocycle is optionally benzofused and is optionally substituted at its nitrogen atoms, if present, with $C_1$–$C_5$ alkyl, phenyl, and benzyl and is optionally substituted at its carbon atoms with $C_1$–$C_5$ alkyl, $C_1$–$C_5$ alkoxy, $C_1$–$C_5$ thioalkoxy, halogen, —$CF_3$, phenyl, benzyl or thienyl; the term includes, 5-membered heterocycles having one heteroatom, for example, thiophenes, pyrroles, furans, benzothiophenes, indoles, benzofurans, and the like; 5-membered heterocycles having two heteroatoms, for example, oxazoles, isoxazoles, pyrazoles, imidazoles, thiazoles, isothiazoles, benzoxazoles, benzopyrazoles, benzimidazoles, benzothiazoles, and the like; 5-membered heterocycles having three heteroatoms, for example, triazoles, thiadiazoles, furazans, and the like; 6-membered heterocycles with one heteroatom, for example, pyridine, quinoline, isoquinoline, and the like; 6-membered heterocycles with two heteroatoms, for example, pyrazines, pyrimidines, pyridazines, quinazolines, dioxanes, quinazolines, cinnolines, benzodioxanes, and the like;

the term "$C_1$–$C_5$ alkyl" refers to a straight or branched chain alkyl having from one to five carbon atoms and includes, methyl, ethyl, n-propyl, iso-propyl, n-butyl, sec-butyl, iso-butyl, t-butyl, pentyl, and the like;

the term "$C_3$–$C_5$ alkenyl" refers to a straight or branched chain alkenyl having from three to five carbon atoms containing at least one double-bond and includes, allyl, 3-methyl-prop-2-enyl, but-2-enyl, but-3-enyl, pent-2-enyl, pent-3-enyl, pent-4-enyl, and the like;

the term "$C_3$–$C_5$ alkynyl" refers to an unsaturated branched or linear group having from three to five carbon atoms and at least one triple bond and includes, propargyl, but-2-ynyl, but-3-ynyl, pentynyl and the like;

the term "$C_1$–$C_5$ alkoxy" refers to a straight or branched chain alkoxy having from one to five carbon atoms and includes, methoxy, ethoxy, n-propoxy, iso-propoxy, n-butoxy, sec-butoxy, iso-butoxy, t-butoxy, pentoxy, and the like;

the term "$C_1$–$C_5$ thioalkoxy" refers to a straight or branched chain thioalkoxy having from one to five carbon atoms and includes, thiomethoxy, thioethoxy, thiopropoxy, thiobutoxy, thiopentoxy, and the like; and the term "pharmaceutically-acceptable addition salt" refers to an acid addition salt.

The compound of formula I and the intermediates described herein form pharmaceutically acceptable acid addition salts with a wide variety of organic and inorganic acids and include the physiologically acceptable salts which are often used in pharmaceutical chemistry. Such salts are also part of this invention. A pharmaceutically-acceptable addition salt is formed from a pharmaceutically-acceptable acid as is well known in the art. Such salts include the pharmaceutically acceptable salts listed in *Journal of Pharmaceutical Science*, 66, 2–19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

As is appreciated by the skilled person, compounds of formula I exist as stereoisomers. The present invention relates to the stereoisomers of the compounds of formula I. Herein, the Cahn-Prelog-Ingold designations of (R)— and (S)— are used to refer to specific isomers where designated. Herein, the designations endo- and exo- are used to designate the relative spatial relationship between the 7-postion and the 2-aza function of the 2-aza-bicyclo[2.2.1]heptane.

The specific endo- and exo-isomers are shown below:

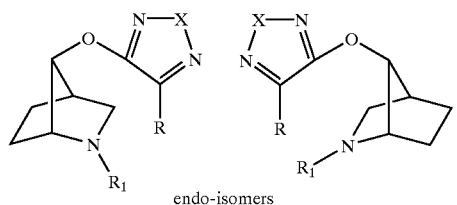

endo-isomers

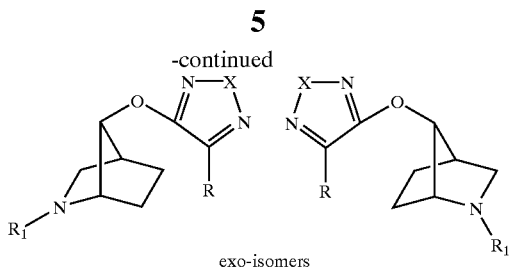

exo-isomers

The specific isomers can by prepared by stereospecific synthesis or can be resolved and recovered by techniques known in the art, such as, chromatography on chiral stationary phases, and fractional recrystallization of addition salts formed by reagents used for that purpose. Useful methods of resolving and recovering specific stereoisomers are known in the art and described in *Stereochemistry of Organic Compounds*, E. L. Eliel and S. H. Wilen (Wiley-Interscience 1994), *Enantiomers, Racemates, and Resolutions*, J. Jacques, A. Collet, and S. H. Wilen (Wiley-Interscience 1981), and European Patent Application No. EP-A-838448, published Apr. 29, 1998.

It is to be understood that the invention extends to each of the isomeric forms of the compounds of the present invention including the geometric, diastereomeric, enantiomeric, and racemic forms of the compound of formula I.

As with any group of pharmaceutically active compounds, some groups are preferred in their end use application.

Preferred embodiments of the present invention are given below:

Compounds wherein X is sulfur are preferred.

Compound wherein $R_1$ is hydrogen are preferred.

Compounds wherein R is —$OR_2$ or —$SR_2$ are preferred.

Compounds wherein R is —$OR_2$ or —$SR_2$ and $R_2$ is $C_1$–$C_{10}$ alkyl are preferred.

Compounds wherein R is —$OR_2$ or —$SR_2$ and $R_2$ is $C_1$–$C_{10}$ alkyl substituted with phenyl or substituted phenyl are preferred.

Compounds wherein R is —$OR_2$ or —$SR_2$ and $R_2$ is $C_1$–$C_{10}$ alkyl substituted with a heterocycle selected from the group consisting of thienyl, furanyl, pyridyl, and benzodioxanyl are preferred.

Compounds having the endo-configuration are most preferred.

Examples of compounds encompassed by the present invention include the following. This list is meant to be representative only and in not intended to limit the scope of the invention in any way:

Endo-2-aza-7-(4-methoxy-1,2,5-thiadiazol-3-yl)oxy)bicyclo[2.2.1]heptane;

Endo-2-aza-7-(4-ethoxy-1,2,5-thiadiazol-3-yl)oxy)bicyclo[2.2.1]heptane;

Endo-2-aza-7-(4-thiomethoxy-1,2,5-thiadiazol-3-yl)oxy)bicyclo[2.2.1]heptane;

Endo-2-aza-7-(4-thioethoxy-1,2,5-thiadiazol-3-yl)oxy)bicyclo[2.2.1]heptane; and

Endo-2-aza-7-(4-thiobenzyl-1,2,5-thiadiazol-3-yl)oxy)bicyclo[2.2.1]heptane.

The compounds of formula I are prepared as described in Reaction Schemes A.1 and A.2 below. In Reaction Scheme A.1 and A.2, all substituents, unless otherwise indicated, are as previously defined. In Reaction Scheme A.1 and A.2 all reagents are well known and appreciated in the art.

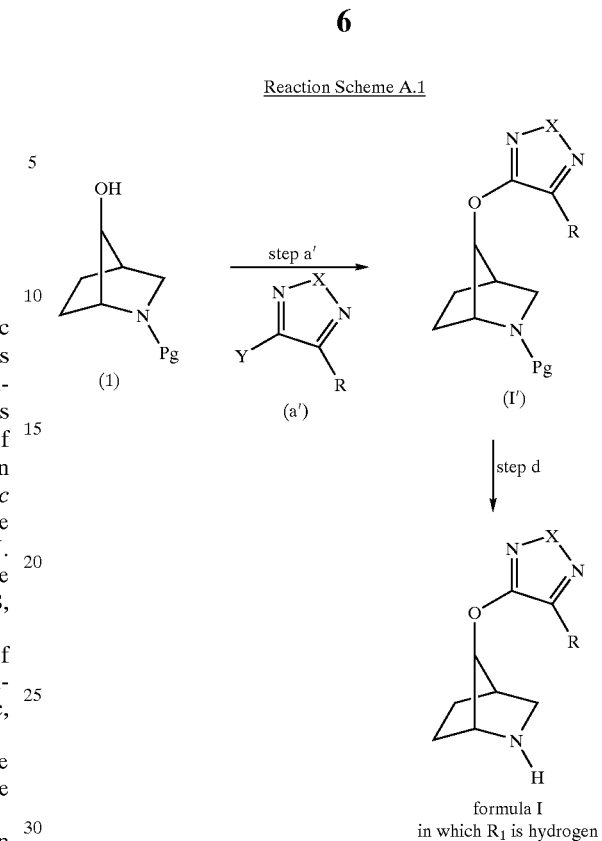

Reaction Scheme A.1 formula I
in which $R_1$ is hydrogen

In Reaction Scheme A.1, step a', depicts the reaction of a suitable alcohol of formula (1) and a suitable compound of formula (a') to give a compound of formula I'. A suitable compound of formula (1) is one in which Pg is a suitable protecting group and $R_1$ is as desired in the final product or gives rise upon alkylation to $R_1$ as desired in the final product of formula I. A suitable compound of formula (1) may also one which has the stereochemistry as desired in the final compound of formula I or one which give rise to the stereochemistry as desired in the final compound of formula I. Suitable protecting group for amines are well known in the art and include benzyl, alkyl substituted benzyl, such as α-methylbenzyl, and carbamates such as benzyloxycarbonyl and t-butoxycarbonyl. A suitable compound of formula (a') is one in which R is as desired in the final product of formula I or gives rise upon sulfide oxidation to R as desired in the final product of formula I. A suitable compound of formula (a') is also one in which Y is a leaving group or a hydroxy group.

For example, a metal alkoxide of a compound of formula (1) and a compound of formula (a') in which Y is a leaving group are contacted to give a compound of formula I'. Suitable compounds of formula (a') having leaving groups, Y, such as chloro, bromo, iodo, alkylsulfonyl, and the like. The preparation of compounds of formula (a') in which Y is a leaving group is well known and appreciated in the art. For example see U.S. Pat. No. 5,821,370 which is hereby incorporated by reference, PCT Publication No. WO 98/54151, published Dec. 3, 1998, and *J. Med. Chem.*, 41, 379–392 (1998). While many metals are suitable for this reaction, generally, an alkali metal alkoxide is used, with the lithium, sodium, and potassium alkoxide being preferred. The alkoxide is formed by contacting of an alcohol of formula (1) with a suitable base, such as lithium hydride, lithium N,N-diisopropylamide, sodium hydride, potassium hydride, and potassium t-butoxide. Typically, the reaction is carried out in a substantially anhydrous, aprotic solvent, such as tetrahydrofuran, diethyl ether, dioxane, N-methylpyrrolidinone, N,N-dimethylformamide, N,N-dimethylacetamide, or dimethylsulfoxide. In general, the reaction is carried out at temperatures of from about −20° C. to about 70° C. The reaction typically requires from about 30 minutes to about 48 hours. The product can be isolated and purified by techniques well known in the art, such as filtration, evaporation, extraction, trituration, chromatography, and crystallization.

Alternately, for example, a compound of formula (1), a compound of formula (a') in which Y is a hydroxy group, a suitable phosphorous(III) compound, and a suitable diester of azodicarboxylate are contacted with under Mitsunobu conditions to give a compound of formula I'. Such reactions of compounds of formula (1) and compounds of formula (a') in which Y is a hydroxy group are well known in the art. See *Synthesis*, 1–28 (1981), U.S. Pat. No. 5,821,370, and PCT Publication No. WO 96/38430, published Dec. 5, 1996. The preparation of compounds of formula (a') is well known and appreciated in the art. Suitable phosphorous(III) compounds include, triphenylphosphine, tri(p-tolyl)phosphine, tributylphosphine, and tri(p-dimethylaminiophenyl)phosphine. Suitable diester of azodicarboxylates include diethyl azodicarboxylate, dimethyl azodicarboxylate, diisopropyl azodicarboxylate. Typically, the reaction is carried out in a substantially anhydrous, aprotic solvent, such as tetrahydrofuran, diethyl ether, or dioxane. In general, the reaction is carried out at temperatures of from about 0° C. to about 50° C. The reaction typically requires from about 30 minutes to about 12 hours. The product can be isolated and purified by techniques well known in the art, such as filtration, evaporation, extraction, trituration, chromatography, and crystallization.

In Reaction Scheme A.1, step d, a protected compound of formula I' is deprotected to give a compound of formula I. Deprotection of amine protecting groups is well known and appreciated in the art. *Protecting Groups in Organic Synthesis*, Theodora Greene (Wiley-Interscience).

In Reaction Scheme A.1, optional step e, not shown, a compound of formula I in which $R_1$ is hydrogen undergoes N-alkylation to give a compound of formula I in which $R_1$ is alkyl, alkenyl, or alkynyl as desired in the final product of formula I and/or a compound of formula I in which R is thioalkyl, thioalkenyl, or thioalkynyl undergoes sulfide oxidation to give a compound of formula I in which R is a sulfoxide or sulfone. Such N-alkylation and oxidation of sulfides are well known and appreciated in the art.

In Reaction Scheme A.1, optional step f, not shown, an acid addition salt is formed using a pharmaceutically-acceptable acid. The formation of acid addition salts is well known and appreciated in the art.

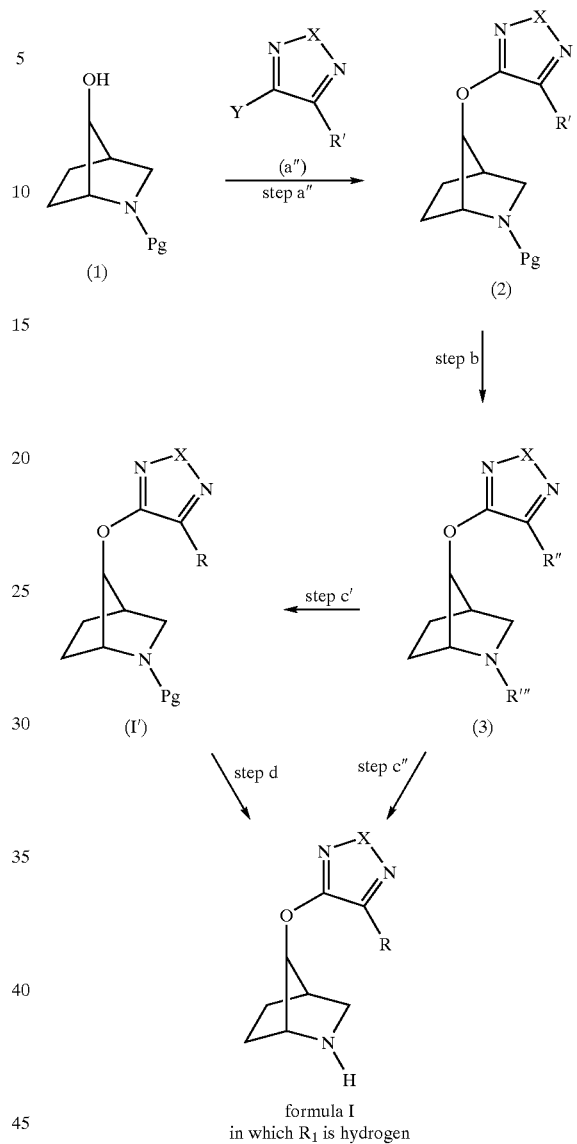

Reaction Scheme A.2 formula I
in which $R_1$ is hydrogen

In Reaction Scheme A.2, step a", depicts the reaction of a suitable alcohol of formula (1) and a suitable compound of formula (a") to give a compound of formula (2). A suitable compound of formula (1) is as described in Reaction Scheme A.1, step a' and a suitable compound of formula (a") is one in which R' is a leaving group or gives rise to a leaving group, R", in Reaction Scheme A.2, step b. A suitable compound of formula (a") is also one in which Y is a leaving group or a hydroxy group. As is appreciated in the art the compound of formula (2) can be deprotected and again protected, using suitable a protecting group, before it is taken on in Reaction Scheme A.2, step b.

The reaction is carried out as taught in Reaction Scheme A.1, step a', using a compound of formula (a") in which Y is hydroxy, chloro, bromo, iodo, alkylsulfonyl, and the like and R' is a leaving group, such as chloro, bromo, iodo, alkylsulfonyl or, preferably, gives rise to a leaving group, such as a thioalkyl group which gives rise to an alkylsulfonyl upon oxidation. Alternately, the reaction is carried out as taught in Reaction Scheme A.1, step a', using a compound of formula (a") in which Y is a hydroxy group and R' is a leaving group, such as chloro, bromo, iodo, alkylsufonyl or, preferably, gives rise to a leaving group, such as a thioalkyl group which gives rise to an alkylsulfonyl upon oxidation.

In Reaction Scheme A.2, step b, a compound of formula (2) in which R' gives rise to a leaving group, R", is converted to a compound of formula (3). As is appreciated by the skilled artisan; where a compound of formula (2) is used in which R' is a thioalkyl group which is oxidized to a compound of formula (3) in which R" is an alkylsulfonyl, the compound of formula (2) can be protected or can be one which has been deprotected. Thus, the compound of formula (3) prepared in this step can be one in which R'" is a suitable protecting group as defined in Reaction Scheme A.1, step a' or can give a compound in which R'" is hydrogen.

For example, a compound of formula (2) in which R' is a thioalkyl group is contacted with a suitable oxidizing agent to give a compound of formula (3) in which R' is an alkylsulfonyl as is well known in the art. For examples see U.S. Pat. No. 5,605,908. Suitable oxidizing agents for this reaction are well known in the art and include oxone®, m-chloroperbenzoic acid, and hydrogen peroxide, oxone®, m-chloroperbenzoic acid, and hydrogen peroxide. Typically, the reaction is carried out in a solvent. Generally, when oxone® or hydrogen peroxide are used the solvent is water or aqueous mixtures. Generally, when m-chloroperbenzoic acid is used the solvent is an organic solvent, such as dichloromethane, chloroform, and the like. In general, the reaction is carried out at temperatures of from about −20° C. to about 50° C. The reaction typically requires from about 30 minutes to about 48 hours. The product can be isolated and purified by techniques well known in the art, such as filtration, evaporation, extraction, trituration, chromatography, and crystallization.

Alternately, as is appreciated by those skilled in the art, a compound of formula (3) is readily prepared from the alkoxide of a compound of formula (1) on 3-chloro-4-alkylsulfonyl-1,2,4-thiadiazole as described in U.S. Pat. No. 5,821,370. Such an approach gives a compound of formula (3) in which R" is chloro and which are suitable for the reaction depicted in Reaction Scheme A.2, step c', below.

In Reaction Scheme A.2, step c', a compound of formula (3) in which R'" is a protecting group is contacted with an suitable metal alkoxide or metal thioalkoxide to give a compound of formula I'. A suitable alkoxide or thioalkoxide is one which give rise to a compound of formula I' in which R is —OR$_2$ or —SR$_2$.

For example, a compound of formula (3) is contacted with an suitable metal alkoxide or metal thioalkoxide to give a compound of formula I'. While many metals are suitable for this reaction, generally, an alkali metal alkoxide or thioalkoxide is used, with the sodium and potassium alkoxide being preferred. The suitable alkoxide or thioalkoxide is formed by contacting an alcohol (HOR$_2$) with a suitable base, such as lithium hydride, sodium hydride, potassium hydride, and potassium t-butoxide or a thiol (HSR$_2$) with a suitable base, such as lithium hydride, sodium hydride, potassium methoxide, sodium methoxide, sodium hydroxide, potassium hydroxide, potassium hydride, and potassium t-butoxide. Typically, the reaction is carried out in a substantially anhydrous, aprotic solvent, such as tetrahydrofuran, dioxane, N-methylpyrrolidinone, N,N-dimethylformamide, N,N-dimethylacetamide, or dimethylsulfoxide. In general, the reaction is carried out at temperatures of from about −20° C. to about 70° C. The reaction typically requires from about 30 minutes to about 48 hours. The product can be isolated and purified by techniques well known in the art, such as filtration, evaporation, extraction, trituration, chromatography, and crystallization.

In Reaction Scheme A.2, step c", a compound of formula (3) in which R'" is hydrogen is contacted with an suitable metal alkoxide or metal thioalkoxide to give a compound of formula I. A suitable alkoxide or thioalkoxide is as defined in Reaction Scheme A.2, step c'.

In Reaction Scheme A.2, step d, a protected compound of formula I' is deprotected as described in Reaction Scheme A.1, step d, above.

In Reaction Scheme A.2, optional step e, not shown, a compound of formula I in which R$_1$ is hydrogen or a compound of formula (3) in which R'" is hydrogen undergoes N-alkylation to give a compound of formula I in which R$_1$ is alkyl, alkenyl, or alkynyl as desired in the final product of formula I and/or a compound of formula I in which R is thioalkyl, thioalkenyl, or thioalkynyl undergoes sulfide oxidation to give a compound of formula I in which R is a sulfoxide or sulfone. Such N-alkylation and oxidations of sulfides are well known and appreciated in the art.

In Reaction Scheme A.2, optional step f, not shown, an acid addition salt is formed using a pharmaceutically-acceptable acid. The formation of acid addition salts is well known and appreciated in the art.

The present invention is further illustrated by the following examples and preparations. These examples and preparations are illustrative only and are not intended to limit the invention in any way.

The terms used in the examples and preparations have their normal meanings unless otherwise designated. For example "° C." refers to degrees Celsius; "N" refers to normal or normality; "M" refers to molar or molarity; "mol" refers to mole or moles; "mmol" refers to millimole or millimoles; "kg" refers to kilogram or kilograms; "g" refers to gram or grams; "mg" refers to milligram or milligrams; "mL" refers milliliter or milliliters; "L" refers to liter or liters; "bp" refers to boiling point; "mp" refers to melting point; "brine" refers to a saturated aqueous sodium chloride solution; "MS" refers to mass spectrometry; "NMR" refers to nuclear magnetic resonance spectroscopy; "TFA" refers to trifluoroacetic acid; "CH$_2$Cl$_2$" refers to dichloromethane; "MeOH" refers to methanol; "NH$_4$OH" refers to a concentrated aqueous ammonia solution; "KOH" refers to potassium hydroxide; "H$_2$O" refers-to water; "HCl" refers to hydrogen chloride; etc.

PREPARATION 1

Preparation of Endo-2-aza-2-benzyl-bicyclo[2.2.1]heptan-7-ol

According to the procedure of J. Am. Chem. Soc., 107, 1768–1769 (1985), cyclopentadiene (61.7 g, 935 mmol) was added to a solution of benzylamine hydrochloride (67.1 g, 467 mmol), 37% aqueous formaldehyde (65.4 mL/654 mmol), and water (190 mL). The solution was stirred at room temperature for three hours. Water (190 mL) was added to the reaction mixture then washed with diethyl ether (2×250 mL). The aqueous layer was basified with solid KOH then extracted with diethyl ether (3×250 mL). The combined extracts were dried over magnesium sulfate then evaporated to yield 2-aza-2-benzylbicyclo[2.2.1]hept-5-ene (79.6 g, 430 mmol).

According to the procedure in Helv. Chim. Acta., 76, 1203–1215 (1993), 2-aza-2-benzylbicyclo[2.2.1]hept-5-ene (30.0 g, 162.2 mmol) in dichloromethane was added dropwise to a solution of bromine (23.2 g, 145.0 mmol) in dichloromethane (50 mL) at 0° C. Stirred at 0° C. for 16 hours. The reaction mixture was evaporated under reduced pressure and the residue was recrystallized from dichloromethane and diethyl ether to yield 3-bromo-2-benzyl-2-azoniatricyclo[2.2.1.0]heptyl bromide (45.9 g, 132.7 mmol).

Red-Al® (65+wt % solution of sodium bis(2-methoxyethoxy)aluminum hydride in toluene) (8.5 mL/28.9 mmol) was added to a solution of 3-bromo-2-benzyl-2-azoniatricyclo[2.2.1.0]heptyl bromide (10.0/28.9 mmol) in tetrahydrofuran (250 mL) cooled to −10° C. After stirring for two hours, the reaction mixture was quenched with a saturated aqueous sodium bicarbonate solution (125 mL) followed by brine (125 mL), and then extracted with ethyl acetate (3×200 mL). The combined organic extracts were dried over sodium chloride and magnesium sulfate then concentrated on a rotary evaporator to yield exo-2-aza-7-bromo-2-benzyl-bicyclo[2.2.1]heptane (7.5 g, 28.2 mmol).

Exo-2-aza-7-bromo-2-benzyl-bicyclo[2.2.1]heptane (33.3 g, 125.2 mmol) and N-methylpyrrolidinone (containing 15% $H_2O$ v/v, 625 mL) were heated at 100° C. After 72 hours, the reaction mixture was cooled to room temperature, diluted with water, basified with aqueous sodium hydroxide, and then extracted with diethyl ether (3×500 mL). The combined diethyl ether extracts were washed with water (4×200 mL), dried over sodium chloride/magnesium sulfate, then concentrated on a rotary evaporator. The residue was purified by preparative HPLC using silica gel and eluting with 10% (10% $NH_4OH$ in ethanol)/90% ethyl acetate to yield the title compound. (14.0 g, 69.0 mmol).

EXAMPLE 1

Endo-2-aza-7-((4-propylthio-1,2,5-thiadiazol-3-yl)oxy)bicyclo[2.2.1]heptane 1.1 Synthesis of Endo-2-aza-2-benzyl-7-((4-propylthio-1,2,5-thiadiazol-3-yl)oxy)bicyclo[2.2.1]heptane Potassium t-butoxide (1.3 g, 11.3 mmol) was added to a solution of endo-2-aza-2-benzyl-bicyclo[2.2.1]heptan-7-ol (2.3 g, 11.3 mmol) in tetrahydrofuran (50 mL) at −78° C. Stirred for 30 minutes where upon 3-chloro-4-propylthio-1,2,5-thiadiazole (2.2 g, 11.3 mmol) (prepared by the method of *J. Med. Chem.*, 41, 379–392 (1998)) in tetrahydrofuran (25 mL). The reaction was stirred at −78° C. for 16 hours then 1 hour at room temperature. The reaction was poured into brine then extracted with ethyl acetate (3×100 mL). The combined organic extracts were washed with brine, dried over magnesium sulfate, then evaporated. The residue was purified by preparative HPLC using silica gel eluting with 50% ethyl acetate in hexanes to yield the title compound (2.4 g, 6.6 mmol).

1.2 Synthesis of Endo-2-aza-7-((4-propylthio-1,2,5-thiadiazol-3-yl)oxy)bicyclo[2.2.1]heptane Vinyl chloroformate (0.36 mL/4.2 mmol) was added to a solution of endo-2-aza-2-benzyl-6-((4-propylthio-1,2,5-thiadiazol-3-yl)oxy)bicyclo[2.2.1]heptane (0.5 g, 1.4 mmol), proton sponge (0.6 g, 2.8 mmol), and 1,2-dichloroethane (30 mL). The reaction was refluxed for 5 hours. The reaction was diluted with diethyl ether (100 mL) then washed with 1N aqueous hydrochloric acid solution (3×50 mL), saturated aqueous sodium bicarbonate solution (50 mL), and then brine (50 mL). The organic layer was dried over magnesium sulfate then evaporated. The residue was taken up in ethanol (20 mL) and ethanol saturated with hydrochloric acid (20 mL) then refluxed for 16 hours. The solution was evaporated, basified with saturated aqueous sodium bicarbonate solution, then extracted with ethyl acetate (3×75 mL). The combined organic extracts were dried over magnesium sulfate then evaporated. The residue was purified by radial chromatography on silica gel eluting with 1% $NH_4OH$/10% ethanol in dichloromethane to yield the title compound which is isolated as the hydrochloride salt (230 mg): mp, 171–172° C.

EXAMPLE 2

Endo-2-aza-7-((4-propylsulfonyl-1,2,5-thiadiazol-3-yl)oxy)bicyclo[2.2.1]heptane 2.1 Synthesis of Endo-2-aza-7-((4-propylsulfonyl-1,2,5-thiadiazol-3-yl)oxy)bicyclo[2.2.1]heptane A solution of Oxone® (2.4 g, 3.9 mmol) in water (30 mL) was added to a solution of endo-2-aza-7-((4-propylthio-1,2,5-thiadiazol-3-yloxy)bicyclo[2.2.1]heptane (0.7 g, 2.6 mmol) in 1N aqueous hydrochloric acid (10 mL) and tetrahydrofuran (10 mL). After 16 hours, saturated aqueous sodium bisulfite solution was added to the reaction, basified with aqueous sodium bicarbonate, then extracted with ethyl acetate (3×75 mL). The combined organic extracts were washed with water, saturated aqueous sodium bicarbonate solution, water, dried over magnesium sulfate, then evaporated to yield the title compound (0.33 g).

EXAMPLE 3

Endo-2-aza-7-(4-propoxy-1,2,5-thiadiazol-3-yl)oxy)bicyclo[2.2.1]heptane 3.1 Synthesis of Endo-2-aza-7-(4-propoxy-1,2,5-thiadiazol-3-yl)oxy)bicyclo[2.2.1]heptane 1-Propanol (0.2 g, 3.3 mmol) was added to a mixture of potassium t-butoxide (0.25 g, 2.2 mmol) and tetrahydrofuran (75 mL). The reaction was stirred for 1 hour at room temperature then cooled to 0° C. Endo-2-aza-7-((4-propylsulfonyl-1,2,5-thiadiazol-3-yl)oxy)bicyclo[2.2.1]heptane (0.33 g, 1.1 mmol) in tetrahydrofuran (25 mL) was added dropwise to the reaction. The reaction was stirred at 0° C. for 5 hours, quenched with brine, then extracted with ethyl acetate (3×75 mL). The organic extracts were dried over sodium chloride/magnesium sulfate then evaporated to yield the title compound which is isolated as the hydrochloride salt (150 mg) mp, 158–159° C.

PREPARATION 2

Preparation of Endo-2-aza-2-(t-butoxycarbonyl)-bicyclo[2.2.1]heptan-7-ol

A solution of endo-2-aza-2-benzyl-bicyclo[2.2.1]heptan-7-ol (6.0 g, 29.6 mmol) in ethanol (140 mL) was hydrogenated with 10% Pd/C (3.0 g) at 60 PSI of hydrogen at room temperature. After 16 hours, the catalyst was filtered off and the filtrate was evaporated. The evaporated filtrate was combined with tetrahydrofuran (100 mL) and $H_2O$ (50 mL) and was cooled to 0° C. The pH was adjusted to 10 with 5N aqueous sodium hydroxide solution. Di-t-butylcarbonate (9.8 g, 45 mmol) was added to the reaction solution while the pH was maintained >10 with 5N aqueous sodium hydroxide solution. The reaction was stirred at 0° C. for four hours, poured into brine, extracted with ethyl acetate (3×150 mL), dried over sodium chloride/sodium sulfate, and then evaporated. The residue was purified by preparative HPLC using silica gel eluting sequentially with 25% to 90% ethyl acetate in hexanes to yield the title compound (4.2 g, 19.7 mmol).

EXAMPLE 4

Endo-2-aza-7-((4-(4,4,4-trifluorobutoxy)-1,2,5-thiadiazol-3-yl)oxy)bicyclo[2.2.1]heptane 4.1 Synthesis of Endo-2-aza-2-(t-butoxycarbonyl)-7-((4-(propylthio)-1,2,5-thiadiazol-3-yl)oxy)bicyclo[2.2.1]heptane Potassium t-butoxide (1.84 g, 16.4 mmol) was added to a solution of endo-2-aza-2-(t-butoxycarbonyl)-bicyclo[2.2.1]

heptan-7-ol (3.5 g, 16.4 mmol) in tetrahydrofuran (100 mL). The reaction was stirred at 0° C. for 20 minutes, cooled to −78° C., then 3-chloro-4-(propylthio)-1,2,5-thiadiazole (3.2 g, 16.4 mmol) in tetrahydrofuran (20 mL) was added to the reaction. After stirring overnight at −78° C., the reaction was poured into brine and extracted with ethyl acetate (3×150 mL). The organic extracts were dried over sodium chloride/magnesium sulfate then evaporated. The residue was purified by preparative HPLC using silica gel eluting with 5 to 50% ethyl acetate in hexanes to yield the title compound (3.5 g, 9.4 mmol).

4.2 Synthesis of Endo-2-aza-2-(t-butoxycarbonyl)-7-((4-propylsulfonyl-1,2,5-thiadiazol-3-yl)oxy)bicyclo[2.2.1]heptane A solution of Oxone® (16.4 g, 26.6 mmol) in water(80 mL) was added to a solution of endo-2-aza-2-(t-butoxycarbonyl)-7-((4-(propylthio)-1,2,5-thiadiazol-3-yl)oxy)bicyclo[2.2.1]heptane (3.5 g, 9.4 mmol) and tetrahydrofuran (80 mL)and stirred at room temperature for 16 hours. Then the reaction mixture was poured into water and extracted with ethyl acetate (3×150 mL). The organic extracts were dried over sodium chloride/sodium sulfate, then evaporated to yield the title compound (3.2 g, 7.9 mmol).

4.3 Synthesis of Endo-2-aza-2-(t-butoxycarbonyl)-7-((4-(4,4,4-trifluorobutoxy)-1,2,5-thiadiazol-3-yl)oxy)bicyclo[2.2.1]heptane Potassium butoxide (0.22 g, 2.0 mmol)was added to a solution of 4,4,4-trifluoro-1-butanol (0.38 g, 3.0 mmol) and tetrahydrofuran (50 mL) at 0° C. The reaction mixture was stirred for 30 minutes at 0° C. and then a solution of endo-2-aza-2-(t-butoxycarbonyl)-7-((4-propylsulfonyl-1,2,5-thiadiazol-3-yl)oxy)bicyclo[2.2.1]heptane (0.4 g, 1.0 mmol) in tetrahydrofuran (25 mL) was added to the reaction. The reaction mixture was stirred for 4 hours at 0° C. and then the reaction mixture was poured into brine and extracted with ethyl acetate (3×100 mL). The organic extracts were dried over magnesium sulfate then evaporated to yield the title compound (0.34 g, 0.8 mmol).

4.4 Synthesis of Endo-2-aza-7-((4-(4,4,4-trifluorobutoxy)-1,2,5-thiadiazol-3-yl)oxy)bicyclo[2.2.1]heptane Trifluoroacetic acid (0.8 mL) was added to a solution of endo-2-aza-2-(t-butoxycarbonyl)-7-((4-(4,4,4-trifluorobutoxy)-1,2,5-thiadiazol-3-yl)oxy)bicyclo[2.2.1]heptane (0.34 g, 0.8 mmol) in methylene chloride (50 mL) at 0° C. The reaction mixture was stirred at 0° C. for two hours then warmed to room temperature and stirred for sixteen hours. The reaction mixture was then concentrated on a rotary evaporator and the residue was basified with aqueous sodium bicarbonate solution then extracted with ethyl acetate (3×75 mL). The combined organic extracts were dried over magnesium sulfate then evaporated to yield the title compound which is isolated as the hydrochloride salt (133 mg): mp, 112–114° C.

EXAMPLE 5

Endo-2-aza-7-((4-butoxy)-1,2,5-thiadiazol-3-yl)oxy)bicyclo[2.2.1]heptane

Butanol (0.022 g, 0.3 mmol) was added to tetrahydrofuran (2 mL), cooled to 0° C., then a solution of potassium t-butoxide (0.036 g, 0.3 mmol) in dry tetrahydrofuran (2 mL). A solution of endo-2-aza-2-(t-butoxycarbonyl)-7-((4-propylsulfonyl-1,2,5-thiadiazol-3-yl)oxy)bicyclo[2.2.1]heptane (0.056 g, 0.15 mmol) in dry tetrahydrofuran (1 mL) was added at 0° C. and allowed to stand for one hour at 0° C. The reaction mixture was warmed to room temperature and stirred. After 16 hours, the reaction mixture was evaporated, diluted with 15% trifluoroacetic acid in chloroform (6 mL), sealed, then allowed to stand at room temperature for 72 hours. The solvent was evaporated then the reaction mixture was taken up in methanol (1 mL) then poured onto a 1 g SAX ion exchange column (prepared by washing with 1N aqueous sodium hydroxide solution(5×5 mL) then methanol (3×4 mL)). The SAX column was eluted with methanol (3×3 mL). The filtrates were then placed onto a 1 g SCX ion exchange column and washed with methanol (3×3 mL). The product was eluted from the SCX column using 25% saturated methanolic HCl in chloroform (4×2 mL). The solvent was evaporated from the product containing fractions to yield the title compound which is isolated as the hydrochloride salt, electrospray mass spec, positive ion mode MS ion=270.

The following compounds were made by the method of EXAMPLE 5 using the appropriate alcohol or thiol:

endo-2-aza-7-((4-hexoxy)-1,2,5-thiadiazol-3-yl)oxy)bicyclo[2.2.1]heptane hydrochloride, MS ion=298;

endo-2-aza-7-((4-cyclopropylmethoxy)-1,2,5-thiadiazol-3-yl)oxy)bicyclo[2.2.1]heptane hydrochloride, MS ion=268;

endo-2-aza-7-((4-cyclobutylmethoxy)-1,2,5-thiadiazol-3-yl)oxy)bicyclo[2.2.1]heptane hydrochloride, MS ion=282;

endo-2-aza-7-((4-(2-cyclopropyl)ethoxy)-1,2,5-thiadiazol-3-yl)oxy)bicyclo[2.2.1]heptane hydrochloride, MS ion=282;

endo-2-aza-7-((4-(2-butyn-1-oxy))-1,2,5-thiadiazol-3-yl)oxy)bicyclo[2.2.1]heptane hydrochloride, MS ion=266;

endo-2-aza-7-((4-(2-phenylethoxy)-1,2,5-thiadiazol-3-yl)oxy)bicyclo[2.2.1]heptane hydrochloride, MS ion=318;

endo-2-aza-7-((4-(2-phenyl-2-cyclopropylethoxy)-1,2,5-thiadiazol-3-yl)oxy)bicyclo[2.2.1]heptane hydrochloride, MS ion=344;

endo-2-aza-7-((4-(2-(4-bromophenoxy)ethoxy)-1,2,5-thiadiazol-3-yl)oxy)bicyclo[2.2.1]heptane hydrochloride, MS ion=413;

endo-2-aza-7-((4-(3-(2-thienylthio)propoxy)-1,2,5-thiadiazol-3-yl)oxy)bicyclo[2.2.1]heptane hydrochloride, MS ion=370;

endo-2-aza-7-((4-(3-(4-fluorophenyl)propoxy)-1,2,5-thiadiazol-3-yl)oxy)bicyclo[2.2.1]heptane hydrochloride, MS ion=350;

endo-2-aza-7-((4-(1,3-difluoroprop-2-oxy)-1,2,5-thiadiazol-3-yl)oxy)bicyclo[2.2.1]heptane hydrochloride, MS ion=292;

endo-2-aza-7-((4-benzyloxy-1,2,5-thiadiazol-3-yl)oxy)bicyclo[2.2.1]heptane hydrochloride, MS ion=304;

endo-2-aza-7-((4-(4-flurorbenzyloxy)-1,2,5-thiadiazol-3-yl)oxy)bicyclo[2.2.1]heptane hydrochloride, MS ion=322;

endo-2-aza-7-((4-(1-methoxy-2-indanoxy)-1,2,5-thiadiazol-3-yl)oxy)bicyclo[2.2.1]heptane hydrochloride, MS ion=360;

endo-2-aza-7-((4-((1,4-benzodioxan-2-yl)methoxy)-1,2,5-thiadiazol-3-yl)oxy)bicyclo[2.2.1]heptane hydrochloride, MS ion=362;

endo-2-aza-7-((4-(butylthio)-1,2,5-thiadiazol-3-yl)oxy)bicyclo[2.2.1]heptane hydrochloride, MS ion=286;

endo-2-aza-7-((4-(hexylthio)-1,2,5-thiadiazol-3-yl)oxy)bicyclo[2.2.1]heptane hydrochloride, MS ion=314;

endo-2-aza-7-((4-(cyclopropylmethylthio)-1,2,5-thiadiazol-3-yl)oxy)bicyclo[2.2.1]heptane hydrochloride, MS ion=284;

endo-2-aza-7-((4-benzylhtio-1,2,5-thiadiazol-3-yl)oxy)bicyclo[2.2.1]heptane hydrochloride, MS ion=320;

endo-2-aza-7-((4-(2-phenylethylthio)-1,2,5-thiadiazol-3-yl)oxy)bicyclo[2.2.1]heptane hydrochloride, MS ion=334; and endo-2-aza-7-((4-(2-cyclopropyl-2-phenylethylthio)-1,2,5-thiadiazol-3-yl)oxy)bicyclo[2.2.1]heptane hydrochloride, MS ion=394.

PREPARATION 3

Preparation of Endo-(1R)-2-azabicyclo[2.2.1]heptan-7-ol

Cyclopentadiene (5.8 mol) followed by 37% aqueous formaldehyde (5.0 mol) was added to a solution of (S)-(−)-1-phenethyl amine hydrochloride (583 g, 3.6 mol), in a minimal amount of water. The solution was stirred at room temperature overnight. The reaction mixture was diluted with water then washed with diethyl ether. The aqueous layer was basified to a pH of 11–12 with solid KOH then extracted with three times with ethyl acetate. The combined ethyl acetate extracts were dried over magnesium sulfate then evaporated to yield crude (+)-(1R,1'S)-2-1'phenylehtyl)-2-azabicyclo[2.2.1]hept-5-ene. The crude material was purified by column chromatography using an eluent of 95/5/0.3 ethyl acetate/methanol/ammonium hydroxide and a load ratio to 30:1 compound to silica gel which yielded (+)-(1R,1'S)-2-1'phenylehtyl)-2-azabicyclo[2.2.1]hept-5-ene (460 g).

Using the procedure of PREPARATION 1 (−)-(1R,1'S)-2-(1'phenylehtyl)-2-azabicyclo[2.2.1]heptan-7-ol (MS ion=218.3, Optical Rotation: $[\alpha]_D^{23}=-17.482$ (c=)) was synthesized from (+)-(1R,1'S)-2-1'phenylehtyl)-2-azabicyclo[2.2.1]hept-5-ene.

Starting with (+)-(1R,1'S)-2-1'phenylehtyl)-2-azabicyclo[2.2.1]hept-5-ene, the procedure of PREPARATION 1 was used to give the title compound.

PREPARATION 4

Preparation of Endo-(1R)-2-(t-butoxycarbonyl)-2-azabicyclo[2.2.1]heptan-7-ol

Prepare according to the method for PREPARATION 2 using endo-(1R)-2-azabicyclo[2.2.1]heptan-7-ol.

PREPARATION 5

Endo-(1R)-2-aza-2-(t-butoxycarbonyl)-7-((4-(propylsulfonyl)-1,2,5-thiadiazol-3-yl)oxy)bicyclo[2.2.1]heptane Prepare according to the procedure of Example 4 using endo-(1R)-2-(t-butoxycarbonyl)-2-azabicyclo[2.2.1]heptan-7-ol.

EXAMPLE 6

The following compounds were made by the method of EXAMPLE 5 using the appropriate alcohol or thiol and endo-(1R)-2-aza-2-(t-butoxycarbonyl)-7-((4-(propylsulfonyl)-1,2,5-thiadiazol-3-yl)oxy)bicyclo[2.2.1]heptane:

endo-(1R) 2-aza-7-((4-hexylthio)-1,2,5-thiadiazol-3-yl)oxy)bicyclo[2.2.1]heptane hydrochloride, MS ion=314;

endo-(1R) 2-aza-7-((4-cyclobutylmethoxy)-1,2,5-thiadiazol-3-yl)oxy)bicyclo[2.2.1]heptane hydrochloride, MS ion=282;

endo-(1R) 2-aza-7-((4-hexoxy)-1,2,5-thiadiazol-3-yl)oxy)bicyclo[2.2.1]heptane hydrochloride, MS ion=298;

endo-(1R) 2-aza-7-((4-butoxy)-1,2,5-thiadiazol-3-yl)oxy)bicyclo[2.2.1]heptane hydrochloride, MS ion=270;

endo-(1R) 2-aza-7-((4-butylthio)-1,2,5-thiadiazol-3-yl)oxy)bicyclo[2.2.1]heptane hydrochloride, MS ion=286;

endo-(1R) 2-aza-7-((4-(3-methylbut-2-enyloxy)-1,2,5-thiadiazol-3-yl)oxy)bicyclo[2.2.1]heptane hydrochloride, MS ion=282;

endo-(1R) 2-aza-7-((4-(2-thienyl)ethoxy)-1,2,5-thiadiazol-3-yl)oxy)bicyclo[2.2.1]heptane hydrochloride, MS ion=324;

endo-(1R) 2-aza-7-((4-(2-thienyl)methoxy)-1,2,5-thiadiazol-3-yl)oxy)bicyclo[2.2.1]heptane hydrochloride, MS ion=310;

endo-(1R) 2-aza-7-((4-(2-thienyl)ethylthio)-1,2,5-thiadiazol-3-yl)oxy)bicyclo[2.2.1]heptane hydrochloride, MS ion=340;

endo-(1R) 2-aza-7-((4-(2-phenylethoxy)-1,2,5-thiadiazol-3-yl)oxy)bicyclo[2.2.1]heptane hydrochloride, MS ion=318;

endo-(1R) 2-aza-7-((4-(2-phenylethylthio)-1,2,5-thiadiazol-3-yl)oxy)bicyclo[2.2.1]heptane hydrochloride, MS ion=334; and endo-(1R) 2-aza-7-((4-((2-cyclopropyl)ethoxy)-1,2,5-thiadiazol-3-yl)oxy)bicyclo[2.2.1]heptane hydrochloride, MS ion=268.

EXAMPLE 7

Exo-2-aza-7-((4-propylthio)-1,2,5-thiadiazol-3-yl)oxy)bicyclo[2.2.1]heptane 7.1 Synthesis of Exo-2-aza-2-benzyl-7-((4-propylthio-1,2,5-thiadiazol-3-yl)oxy)bicyclo[2.2.1]heptane Triphenyl phosphine (0.6 g/2.3 mmol) and 3-hydroxy-4-propylthio-1,2,5-thiadiazole (0.4 g/2.3 mmol) (prepared by the method of *J. Med. Chem.*, 41, 379–392 (1998)) in tetrahydrofuran (10 mL) were cooled in an ice water bath. Diethyl azodicarboxylate (0.4 g/2.3 mmol) was added dropwise to the reaction mixture then stirred for five minutes. A solution of endo-2-aza-2-benzyl-bicyclo[2.2.1]heptan-7-ol (0.4 g/2.3 mmol) in tetrahydrofuran (10 mL) was added to the reaction. The cooling bath was removed and the reaction was stirred at room temperature for sixteen hours. The solvent was removed under vacuum, the residue was taken up in an aqueous 1N hydrochloric acid solution then extracted with ethyl acetate (2×10 mL). The ethyl acetate extracts were basified with saturated aqueous bicarbonate solution, dried over sodium chloride and sodium sulfate, filtered then evaporated under vacuum to give a residue. The residue was purified by chromatography on silica gel eluting with a gradient of 0.1% concentrated aqueous ammonium/1.0% ethanol to 1% conc. ammonium hydroxide/10% ethanol in chloroform to yield the title compound which was isolated as the oxalate salt. Recrystallization from ethanol/ethyl acetate gave the title compound: mp=160–162° C.

The present invention provides a method of treating diseases and conditions treated by muscarinic receptor modulators in a patient in need thereof comprising administering to the patient an effective amount of a compound of formula I or pharmaceutically-acceptable addition salt thereof. Such diseases and conditions treated by muscarinic receptor modulators include Alzheimer's disease, glaucoma, psychosis, mania, pain, bipolar disorder, depression, sleeping disorders, epilepsy, gastrointestinal motility disorders, urinary incontinence, schizophrenia and schizophreniform conditions, and cognitive enhancement. As agonists of the muscarinic M-4 receptor the compounds of formula I are particularly useful for treating Alzheimer's disease, psychosis, pain, schizophrenia and schizophreniform conditions and enhancing cognition.

The present invention also provides pharmaceutical compositions comprising a compound of formula I and a pharmaceutically acceptable diluent. That is, the present invention provides for the use of a pharmaceutical compositions comprising a compound of formula I and a pharmaceutically acceptable diluent for the treatment various diseases and conditions, for example, Alzheimer's disease, glaucoma, mania, bipolar disorder, depression, sleeping disorders, epilepsy, gastrointestinal motility disorders, urinary incontinence, pain, psychosis, particularly schizophrenia or schizophreniform conditions, and cognition enhancement, such as enhancement of learning, association, consolidation, and recognition.

The term "patient" refers to a mammal afflicted with one or more diseases or conditions treated by muscarinic receptor modulators and includes, mice, rats, dogs, sheep, guinea pigs, cats, monkeys, apes, and humans, etc. or multiple administration to the patient, is effective in alleviating or controlling the treated disease or condition.

An effective amount can be readily determined by the attending diagnostician, as one skilled in the art, by the use of conventional techniques and by observing results. In determining an effective amount, the dose, a number of factors are considered by the attending diagnostician, including, but not limited to: the species of mammal; its size, age, and general health; the specific disorder involved; the degree of involvement or the severity of the disorder; the response of the individual patient; the mode of administration; the bioavailability of the formulation administered; the dose regimen selected; the preference and experience of the attending diagnostician; and other factors known in the art.

The compounds of the invention are effective over a wide dosage range. For example, dosages from about 0.05 mg/kg/day to about 100 mg/kg/day may be given. In humans, preferably from about 0.1 to about 100 mg, per day may be used with a most preferable dosage of about 0.1 mg to about 70 mg per day. In choosing a regimen for patients suffering from diseases and conditions of the central nervous system involving muscarinic receptors it may frequently be necessary to begin with a dosage of from about 20 to about 70 mg per day and when the condition is under control to reduce the dosage as low as from about 0.1 to about 10 mg per day.

The pharmaceutical compositions of the present invention can be administered by a variety of routes including oral and parenteral. The route of administration may be any route, which effectively transports the active compound to the appropriate or desired site of action, such as orally, rectal, transdermal, depot, subcutaneous, intravenous, intramuscular or intranasal.

In administering compound of formula I, generally, it is mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatin capsules, suppositories, sterile injectable solutions, and sterile packaged powders. Some examples of suitable excipients include dextrose, sucrose, lactose, sorbitoli mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, silicon oil, and mineral oil; wetting agents; emulsifying and suspending agents; preserving agents such as methyl- and propylhydroxybenzoates; sweetening agents; and flavoring agents. The compositions can be formed by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

In order to more fully illustrate the operation of this invention, the following formulation examples are provided. The examples are illustrative only, and are not intended to limit the scope of the invention in any way.

FORMULATION 1

A typical tablet, appropriate for use in this method, may be prepared using conventional techniques and may contain:

|  | Amount per Tablet | Concentration by Weight (%) |
| --- | --- | --- |
| Compound of formula I | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg Ph. Eur. | 0.3 |
| TOTAL | 105.45 mg | 100 |

FORMULATION 2

Hard gelatin capsules may be prepared using the following ingredients:

|  | Amount per Tablet | Concentration by Weight (%) |
| --- | --- | --- |
| Compound of formula I | 0.1 mg | 0.05 |
| starch dried | 200 mg | 95.2 |
| magnesium stearate | 10 mg | 4.8 |
| TOTAL | 210.1 mg | 100 |

The above ingredients are mixed and filled into hard gelatin capsules in 210.1 mg quantities.

FORMULATION 3

Suspensions each containing 1 mg of medicament per 5 mL dose are as follows:

|  | Amount per 5 mL of suspension |
| --- | --- |
| Compound of formula I | 1 mg |
| sodium carboxymethyl cellulose | 50 mg |
| syrup | 1.25 mL |
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The binding to muscarinic receptors can be readily determined by those skilled in the art. See *Molecular Pharmacology* 35:469–476 (1989) and *Annu. Rev. Pharmacol. Toxicol.*, 30:633–673 (1990). The binding at the M-4 muscarinic receptor can be determined by the assay below.

EXAMPLE A

Cyclic AMP Accumulation in Pertussis Toxin-treated CHO M-4 Cells

According to the method of *Molecular Pharmacology* 35:469–476 (1989), CHO K1 cells transfected with human M-4 muscarinic receptors were grown to near confluency in T-150 flasks using Dulbecco's Modified Eagle Medium (DMEM) containing 10% fetal bovine serum. Cells were detached with 0.05% trypsin, 0.53 mM EDTA, and were suspended in medium containing 100 ng/ml pertussis toxin. Cells were plated at 30,000 cells per well into 96 well plates. Eighteen to twenty hours later the medium was removed and the cells were washed with serum-free medium. Attached cells were incubated at 37° C. for one hour after addition of 100 µl of serum free DMEM containing 1 mM 3-isobutyl-1-methylxanthine and 1 µM forskolin plus or minus drugs being tested. Incubations were terminated with 200 µl per well of serum free DMEM containing 0.3% triton-X-100. After stopping incubations the plates were allowed to sit for 20 minutes to extract cAMP and samples were then diluted 2.5-fold and were assayed using the scintillation proximity assay of Amersham (Arlington Heights, Ill.).

We claim:

1. A compound of the formula

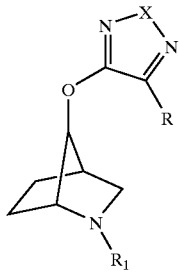

wherein
the compound has the endo-configuration
X is sulfur;
R is —OR$_2$, or —SR$_2$
wherein R$_2$ is C$_1$–C$_{10}$ alkyl substituted with from 1 to 3 substituents selected from the group consisting of hydrogen, halogen,
—CF$_3$, phenyl; optionally substituted with from 1 to 2 substituents independently selected from the group consisting of hydrogen, halogen, C$_1$–C$_5$ alkyl, C$_1$–C$_5$ alkoxy, —CF$_3$; C$_3$–C$_8$ cycloalkyl, thienyl, and —Z-thienyl, wherein Z is oxygen or sulfur;
R$_1$ is hydrogen;
or a pharmaceutically acceptable salt thereof.

2. A compound of claim 1 wherein R$_2$ is C$_1$–C$_{10}$ alkyl substituted with 3 hydrogens.

3. A compound of claim 1 wherein the compound is selected from the group consisting of
endo-2-aza-7-((4-propylthio-1,2,5-thiadiazol-3-yl)oxy)bicyclo[2.2.1]heptane;
endo-2-aza-7-(4-propoxy-1,2,5-thiadiazol-3-yl)oxy)bicyclo[2.2.1]heptane;
endo-2-aza-7-((4-(4,4,4-trifluorobutoxy)-1,2,5-thiadiazol-3-yl)oxy)bicyclo[2.2.1]heptane;
endo-2-aza-7-((4-butoxy-1,2,5-thiadiazol-3-yl)oxy)bicyclo[2.2.1]heptane;
endo-2-aza-7-((4-hexoxy)-1,2,5-thiadiazol-3-yl)oxy)bicyclo[2.2.1]heptane;
endo-2-aza-7-((4-cyclopropylmethoxy)-1,2,5-thiadiazol-3-yl)oxy)bicyclo[2.2.1]heptane;
endo-2-aza-7-((4-cyclobutylmethoxy)-1,2,5-thiadiazol-3-yl)oxy)bicyclo[2.2.1]heptane;
endo-2-aza-7-((4-(2-cyclopropyl)ethoxy)-1,2,5-thiadiazol-3-yl)oxy)bicyclo[2.2.1]heptane;
endo-2-aza-7-((4-(2-phenylethoxy)-1,2,5-thiadiazol-3-yl)oxy)bicyclo[2.2.1]heptane;
endo-2-aza-7-((4-(2-phenyl-2-cyclopropylethoxy)-1,2,5-thiadiazol-3-yl)oxy)bicyclo[2.2.1]heptane;
endo-2-aza-7-((4-(2-(4-bromophenoxy)ethoxy)-1,2,5-thiadiazol-3-yl)oxy)bicyclo[2.2.1]heptane;
endo-2-aza-7-((4-(3-(2-thienylthio)propoxy)-1,2,5-thiadiazol-3-yl)oxy)bicyclo[2.2.1]heptane;
endo-2-aza-7-((4-(3-(4-fluorophenyl)propoxy)-1,2,5-thiadiazol-3-yl)oxy)bicyclo[2.2.1]heptane;
endo-2-aza-7-((4-(1,3-difluoroprop-2-oxy)-1,2,5-thiadiazol-3-yl)oxy)bicyclo[2.2.1]heptane;
endo-2-aza-7-((4-benzyloxy-1,2,5-thiadiazol-3-yl)oxy)bicyclo[2.2.1]heptane;
endo-2-aza-7-((4-(4-flurorbenzyloxy)-1,2,5-thiadiazol-3-yl)oxy)bicyclo[2.2.1]heptane;
endo-2-aza-7-((4-(butylthio)-1,2,5-thiadiazol-3-yl)oxy)bicyclo[2.2.1]heptane;
endo-2-aza-7-((4-(hexylthio)-1,2,5-thiadiazol-3-yl)oxy)bicyclo[2.2.1]heptane;
endo-2-aza-7-((4-(cyclopropylmethylthio)-1,2,5-thiadiazol-3-yl)oxy)bicyclo[2.2.1]heptane;
endo-2-aza-7-((4-benzylhtio-1,2,5-thiadiazol-3-yl)oxy)bicyclo[2.2.1]heptane;
endo-2-aza-7-((4-(2-phenylethylthio)-1,2,5-thiadiazol-3-yl)oxy)bicyclo[2.2.1]heptane;
endo-2-aza-7-((4-(2-cyclopropyl-2-phenylethylthio)-1,2,5-thiadiazol-3-yl)oxy)bicyclo[2.2.1]heptane;
endo-(1R) 2-aza-7-((4-hexylthio)-1,2,5-thiadiazol-3-yl)oxy)bicyclo[2.2.1]heptane;

endo-(1R) 2-aza-7-((4-cyclobutylmethoxy)-1,2,5-thiadiazol-3-yl)oxy)bicyclo [2.2.1]heptane;

endo-(1R) 2-aza-7-((4-hexoxy)-1,2,5-thiadiazol-3-yl)oxy)bicyclo[2.2.1]heptane;

endo-(1R) 2-aza-7-((4-butoxy)-1,2,5-thiadiazol-3-yl)oxy)bicyclo[2.2.1]heptane;

endo-(1R) 2-aza-7-((4-butylthio)-1,2,5-thiadiazol-3-yl)oxy)bicyclo[2.2.1]heptane;

endo-(1R) 2-aza-7-((4-(2-thienyl)ethoxy)-1,2,5-thiadiazol-3-yl)oxy)bicyclo[2.2.1]heptane;

endo-(1R) 2-aza-7-((4-(2-thienyl)methoxy)-1,2,5-thiadiazol-3-yl)oxy)bicyclo[2.2.1]heptane;

endo-(1R) 2-aza-7-((4-(2-thienyl)ethylthio)-1,2,5-thiadiazol-3-yl)oxy)bicyclo[2.2.1]heptane;

endo-(1R) 2-aza-7-((4-(2-phenylethoxy)-1,2,5-thiadiazol-3-yl)oxy)bicyclo[2.2.1]heptane;

endo-(1R) 2-aza-7-((4-(2-phenylethylthio)-1,2,5-thiadiazol-3-yl)oxy)bicyclo[2.2.1]heptane; and endo-(1R) 2-aza-7-((4-((2-cyclopropyl)ethoxy)-1,2,5-thiadiazol-3-yl)oxy)bicyclo[2.2.1]heptane.

4. A pharmaceutical compositions comprising a compound of claim 1 and a pharmaceutically acceptable diluent.

5. A pharmaceutical compositions comprising a compound of claim 2 and a pharmaceutically acceptable diluent.

6. A method of treating Alzheimer's disease, comprising administering to a patient in need thereof an effective amount of a compound of claim 1.

7. A method of treating Alzheimer's disease, comprising administering to a patient in need thereof an effective amount of a compound of claim 2.

8. A method of treating pain, comprising administering to a patient in need thereof an effective amount of a compound of claim 1.

9. A method of treating pain, comprising administering to a patient in need thereof an effective amount of a compound of claim 2.

* * * * *